(12) United States Patent
Dennis

(10) Patent No.: US 6,228,095 B1
(45) Date of Patent: May 8, 2001

(54) SPECIMEN RETRIEVAL DEVICE

(75) Inventor: William G. Dennis, Jacksonville, FL (US)

(73) Assignee: Core Dynamics, Inc., Jacksonville, FL (US)

( * ) Notice: Subject to any disclaimer, the term of this patent is extended or adjusted under 35 U.S.C. 154(b) by 0 days.

(21) Appl. No.: 09/417,673

(22) Filed: Oct. 14, 1999

(51) Int. Cl.⁷ .................................................. A61B 17/00
(52) U.S. Cl. ............................................................ 606/114
(58) Field of Search .................................. 606/114, 113, 606/110, 127; 604/27, 275; 128/DIG. 24

(56) References Cited

U.S. PATENT DOCUMENTS

| | | |
|---|---|---|
| 4,557,255 | 12/1985 | Goodman . |
| 4,590,936 * | 5/1986 | Straub et al. ........................ 606/114 |
| 5,037,379 | 8/1991 | Clayman et al. . |
| 5,143,082 | 9/1992 | Kindberg et al. . |
| 5,147,371 | 9/1992 | Washington et al. . |
| 5,190,555 | 3/1993 | Wetter et al. . |
| 5,215,521 | 6/1993 | Cochran et al. . |
| 5,279,539 | 1/1994 | Bohan et al. . |
| 5,312,416 | 5/1994 | Spaeth et al. . |
| 5,341,815 | 8/1994 | Cofone et al. . |
| 5,352,184 | 10/1994 | Goldberg et al. . |
| 5,354,303 | 10/1994 | Spaeth et al. . |
| 5,465,731 | 11/1995 | Bell et al. . |
| 5,647,372 | 7/1997 | Tovey et al. . |
| 5,681,324 | 10/1997 | Kammerer et al. . |
| 5,759,187 | 6/1998 | Nakao et al. . |
| 6,059,793 * | 5/2000 | Pagedas ............................... 606/114 |

* cited by examiner

Primary Examiner—Manuel Mendez
(74) Attorney, Agent, or Firm—McGuireWoods, LLP

(57) ABSTRACT

A device and method for retrieving specimens from a body cavity during minimally invasive surgery uses a specimen pouch that is deployable from an introducer inserted into the body cavity through a predefined passage such as a cannula. The specimen pouch includes a resilient band that causes the specimen pouch to open automatically and remain open after removal from the introducer. Once removed from the introducer, the specimen pouch is free-standing with no attachment to the introducer or to an externally operated closure mechanism. Closure and removal are accomplished using a conventional forceps or other instrument to grasp a portion of the band and withdraw the band and the opening of the pouch into the introducer. The pouch is configured so that withdrawal of the band into the introducer causes the material around the opening of the pouch to gather and seal the opening.

12 Claims, 8 Drawing Sheets

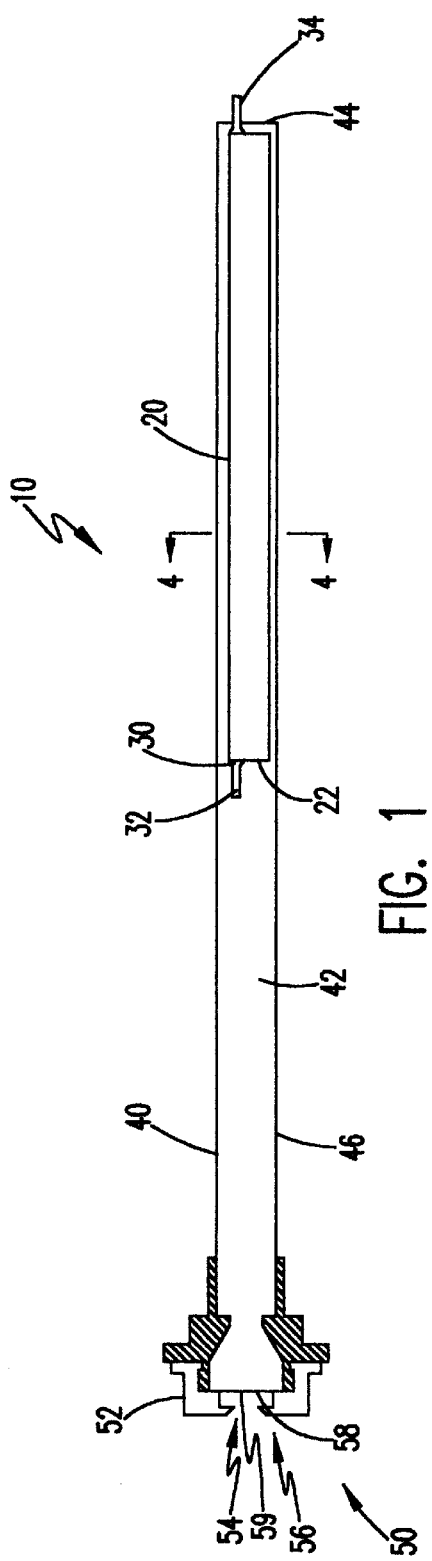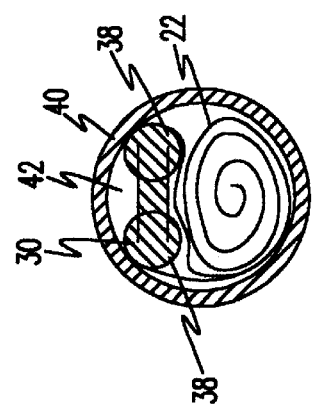

SPECIMEN RETRIEVAL DEVICE

BACKGROUND OF THE INVENTION

The present invention relates broadly to surgical instruments and more particularly to methods and a device for collecting and removing specimens from a body cavity during surgery.

During surgery, there is often a need for the collection and removal of tissue specimens, such as organs or other material from a body cavity of the patient. These materials must generally be isolated to prevent contamination of the body cavity during removal. In minimally invasive surgery where access to the body cavity is restricted to vary small incisions, isolation and removal of specimens can be difficult. This is particularly so because such surgery often involves insufflation of the body cavity requiring that the access incisions be sealed against leakage.

The problem of specimen retrieval during minimally invasive surgery has typically been addressed by the introduction of a closable, flaccid bag or pouch into the body cavity. This pouch is typically deployed through a cannula and includes an arrangement for remotely closing the bag once a specimen has been deposited therein. Once closed, the pouch may be withdrawn through the cannula.

Several problems have been presented by previous specimen pouch designs, particularly with respect to their closure mechanisms. Because a specimen pouch must be closed prior to removal from the body cavity, its closure mechanism must be, in part, external to the patient's body. The mechanism often takes the form of a tether, drawstring or other flexible member that is threaded around the bag opening and through the cannula. Closure is typically accomplished by retraction of this member which results in the cinching of the pouch. With most such designs, the pouch must remain attached to this mechanism or to the cannula used to introduce the pouch. In either case, the introducer cannula must remain in place, typically with a portion of the closure mechanism disposed therein. This not only prevents the cannula from being used for other instruments, it restricts the movement of the pouch within the body cavity.

Another problem results from the manner in which the closure mechanism draws the pouch closed. Closure is usually accomplished using a form of cinch or noose wherein a drawstring or belt is drawn through a sleeve disposed around the opening of the pouch. This method often results in irregular bunching of the material around the pouch access opening which, in turn, can result in incomplete closure and an unacceptable risk of contamination. Further, nooses and other mechanisms used for closure require the drawing of a single strand or belt through essentially the complete circumference of a sleeve surrounding the bag opening. In addition to compounding the bunching problem, this results in an increase in the force required to draw the strand or belt through the sleeve as the bag nears complete closure.

Other specimen bag designs have attempted to solve the closure problem by using collapsible spring members or other relatively complex mechanisms that may require the use of specialized instruments to assist in closure.

There is accordingly a need for a specimen retrieval device that provides secure isolation of collected specimens using a low complexity, remotely manipulated closure mechanism that is separable from the collection device.

SUMMARY OF THE INVENTION

It is accordingly an object of the present invention to provide an improved specimen retrieval device for use in minimally invasive surgery.

It is a further object of the present invention to provide an improved specimen retrieval device that includes a specimen pouch stored in an introducer and insertable into a body cavity through a cannula.

It is also an object of the present invention to provide a specimen pouch that is initially stored in a storage configuration and automatically opens to deployed configuration when removed from storage.

It is yet another object of the present invention to provide a specimen pouch that, once deployed, is separate and independent from the other elements of the invention used to facilitate insertion, closure and retrieval of the pouch.

Another object of the present invention is to provide a specimen pouch having a closure mechanism that is operable using conventional surgical instruments.

It is also an object of the present invention to provide a specimen pouch closure mechanism that securely closes the pouch while reducing the risk of leakage due to bunching of the material surrounding the bag opening.

It is a further object of the present invention to provide a method for collecting and removing specimens from a body cavity using a specimen retrieval device according to the present invention.

To those ends, a specimen retrieval device according to the present invention for use within a body cavity during surgery includes an introducer having a proximal end and a distal end and defining a lumen therethrough. The introducer is configured and dimensioned for at least partial introduction into the body cavity through a predefined passageway. The specimen retrieval device further includes a pouch having an access opening defined therein. This pouch is collapsible for storage within the lumen and expandable upon removal from the lumen. The pouch has a first sleeve formed along a first portion of the pouch adjacent the opening and a second sleeve formed along a second portion of the pouch adjacent the opening. These sleeves are configured to define spacings between the sleeves. The specimen retrieval device also includes a resilient band having a first band portion slidably disposed within the first sleeve and a second band portion slidably disposed within the second sleeve. The band is configured to be collapsible for storage within the lumen along with the pouch. The band is also configured to bias the pouch in an open configuration when the pouch is removed from the lumen.

The band of a specimen retrieval device according to the present invention preferably includes at least one grasping tab projecting radially outward from the band. The at least one grasping tab is disposed in one of the spacings and forms a grasping surface for acquisition of the band by a surgical instrument. The band preferably includes first and second grasping tabs disposed in a space relationship along the band and dividing the band into first and second segments intermediate the grasping tabs. The first segment includes the first band portion and the second segment includes the second band portion.

A specimen retrieval device according to the present invention preferably further includes an arrangement for sealing a surgical instrument inserted into the lumen for interaction with the pouch. The arrangement for sealing is preferably attached to the proximal end of the introducer and preferably includes a septum valve.

A method for retrieval of specimens from a body cavity through a predefined passage according to the present invention includes providing a specimen retrieval device. The specimen retrieval device includes an introducer having a proximal end and a distal end and a specimen pouch defining an access opening. The specimen pouch has a first sleeve formed along a first portion of the pouch adjacent the opening and a second sleeve formed along a second portion of the pouch adjacent the opening. The specimen pouch also has a resilient band having a first band portion slidably disposed within the first sleeve and a second band portion slidably disposed within the second sleeve. The band is configured to bias the specimen pouch in an open configuration and includes at least one grasping tab. The specimen pouch is provided in a collapsed configuration and is removably disposed within the introducer adjacent the distal end.

The method for retrieval of specimens further includes the step of inserting the introducer into the predefined passage so that the distal end of the introducer extends through the cannula into the body cavity. The method further includes removing the specimen pouch from the introducer within the body cavity and placing material in the specimen pouch for removal from the body cavity. Also included in the method are the steps of acquiring the band using a surgical instrument, withdrawing the band into the introducer through the distal end, thereby gathering the sleeves and closing the opening of the pouch, and withdrawing the introducer and the specimen pouch through the predefined passage.

In the method for retrieval of specimens according to the present invention, the step of removing the specimen pouch from the introducer preferably includes the step of inserting an instrument into the proximal end of the introducer. The step of removing the specimen pouch also further includes the step of pushing the specimen pouch out of the distal end of the introducer thereby releasing the band to open the specimen pouch and allowing the specimen pouch to assume a deployed configuration within the body cavity.

In a preferred embodiment of the method for retrieval of specimens according to the present invention, the specimen pouch is disposed within the introducer so that one of the at least one grasping tab is disposed adjacent the distal end. In this embodiment, the step of removing the specimen pouch from the introducer preferably includes the steps of inserting a grasping element of a grasping instrument through a second predefined passage into the body cavity, acquiring one of the at least one grasping tab of the band using the grasping element, and pulling the specimen pouch out of the distal end of the introducer using the grasping instrument. This releases the band to open the specimen pouch and allows the specimen pouch to assume a deployed configuration within the body cavity. The step of removing the specimen pouch also further includes the step of releasing the at least one grasping tab.

The step of acquiring the band using a surgical instrument preferably includes the steps of inserting a grasping element of the surgical instrument through the introducer into the body cavity and acquiring one of the at least one grasping tab of the band using the grasping element. The step of withdrawing the band into the introducer preferably includes withdrawing the grasping element into the distal end of the introducer so that the first and second segments of the band make contact with the distal end of the introducer. The step of withdrawing preferably further includes further withdrawing the grasping element toward the proximal end of the introducer, thereby forcing the first and second segments to deform and be pulled into the distal end of the introducer. This causes the distal end of the introducer to make contact with the first and second sleeves, thereby causing the first and second sleeves to slide along the first and second segments away from the one of the at least one grasping tab. This in turn causes the opening of the specimen pouch to close. The step of withdrawing the band also preferably includes still further withdrawing the grasping element toward the proximal end of the introducer, thereby drawing the sleeves into the introducer.

By the above, the present invention provides an effective device and method for the collection and removal of tissue or other material during surgery. The device offers a simple solution to the problem of leakage due to bunching of material around the bag opening. Further the specimen pouch of the present invention is not tied to its introducer or external closure mechanism in any way while in use for specimen collection. The pouch uses a simple closure mechanism that is easy to use and requires no specialized grasping instruments.

BRIEF DESCRIPTION OF THE DRAWING

FIG. 1 is a side cutaway diagrammatic view of a specimen retrieval device according to a preferred embodiment of the present invention;

FIG. 4 is a cross-sectional diagrammatic view of the specimen retrieval device taken at 4—4 of FIG. 1;

DESCRIPTION OF THE PREFERRED EMBODIMENT

Figure 2:
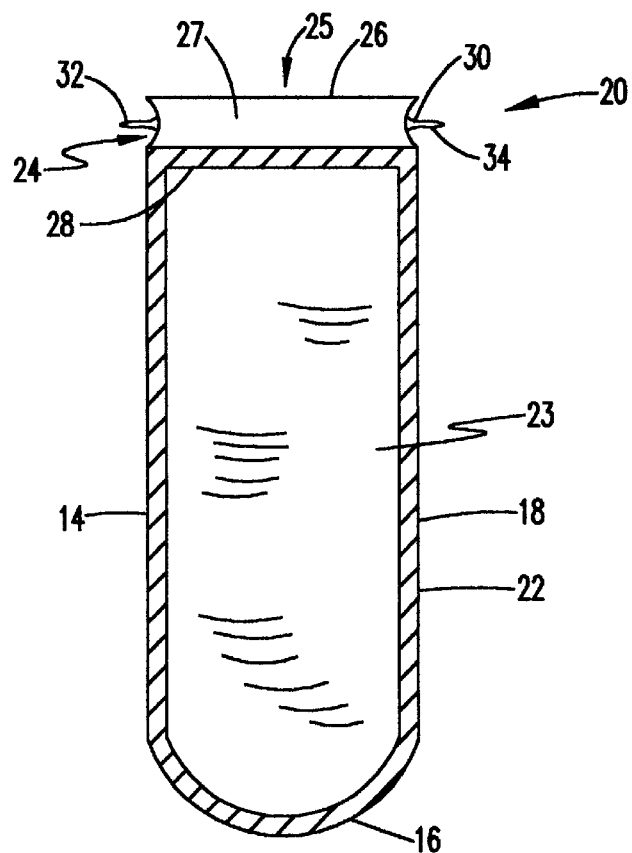
FIG. 2 is a side cutaway diagrammatic view of a deployed pouch assembly of the specimen retrieval device illustrated in FIG. 1.

Turning now to the drawings and more particularly to FIG. 1, a specimen retrieval device according to the preferred embodiment of the present invention is illustrated generally at 10 and includes a pouch assembly 20, an introducer 40 and a valve assembly 50. The specimen retrieval device 10 is intended for use as a repository for material to be removed from a body cavity during minimally invasive surgery. The pouch assembly 20 is initially stored in the introducer 40, which may be partially inserted into the body cavity through a cannula (not shown). The pouch assembly is then removed from the introducer 40 within the body cavity.

The pouch assembly 20 includes a pouch 22 and a band 30 that are collapsible for storage within the introducer 40 and that automatically deploy upon removal from the introducer 40. The deployed pouch assembly 20 is then available for use by the surgeon. The pouch assembly 20 requires no tether or other connection to the introducer 40 or any other instruments disposed within or without the body cavity. For removal, the pouch assembly 20 may be closed and secured to the introducer or other cannula using any suitable grasping instrument as will be described in detail hereafter. The introducer 40 or cannula may then be withdrawn along with the secured pouch assembly 20.

Figure 3:
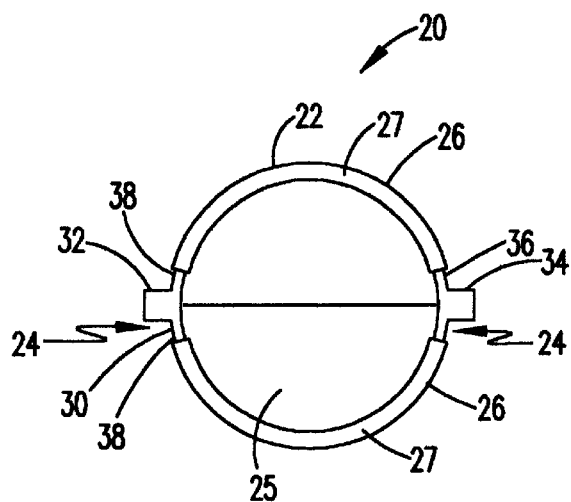
FIG. 3 is a diagrammatic top view of the pouch assembly illustrated in FIG. 2.

Turning now to FIGS. 2 and 3, the pouch assembly 20 includes a pouch 22 and a band 30. The pouch 22 is formed from two pliant, generally planar walls 23, which are preferably formed of a thin, urethane film. These walls 23 are substantially rectangular and are joined along three edges 14, 16, 18 to form an envelope with an opening 25 surrounded by the remaining free edges 28. It will be understood by those having ordinary skill in the art that other envelope shapes may be used such as tapered or hourglass shapes without departing from the spirit of the present invention. The pouch 22 may alternatively be configured as a three dimensional shape such as a cone or prism. It will also be understood that the joined edges 14, 16, 18 of the walls 23 may be welded, fused or bonded in any suitable fashion.

A sleeve 26 is formed from a generally rectangular portion of planar urethane material 27 attached to each free edge 28 of each wall 23. This material 27 is preferably integrally formed with the wall 23, but may also be welded, fused or bonded to the wall 23. The sleeve 26 is formed by looping the material 27 over a portion 38 of the band 30, which will be described in detail hereafter, and joining the material 27 to the wall 23 adjacent the previously free edge 28, thereby slidably disposing the band portion 38 within the sleeve 26. The ends 29 of sleeve 26 are formed so that they have a concave profile as shown in FIG. 2. The concave portions form a space 24 between the two sleeves 26 for grasping of the band 30 or for grasping tabs connected to the band 30 to extend between the sleeves 26. Alternatively, the sleeves 28 can be formed so that they do not extend along the entire length of the free wall edges 28, thus leaving a gap where the two edges 28 come together. It should be noted that FIG. 2 illustrates only one side of the pouch 22 and therefore illustrates only one of the two walls 23 and one of the two sleeves 26. It will be understood by those having ordinary skill in the art that the second wall 23 and the second sleeve 26 are mirror images of the illustrated wall 23 and sleeve 26.

The band 30 is formed with first and second grasping tabs 32 and 34 attached to its outer circumference at diametrically opposed locations as shown in FIG. 3. As described above and as shown in FIGS. 2 and 3, each sleeve 26 is formed so that a portion of the band 30 is slidably disposed within the sleeve 26 between the two grasping tabs 32, 34. The concave configuration of the sleeve ends 29 provides a space 24 between the sleeves through which the grasping tabs 32, 34 extend. The band 30 and grasping tabs 32, 34 are preferably integrally formed of polypropylene. the material and dimensions for the band 30 are selected so that it is collapsible for storage within the introducer 40 along with the pouch 22 yet has sufficient resilience and stiffness so that the band 30 will cause the pouch 22 to open and remain open when the pouch assembly 20 is removed from the introducer 40. The band is preferably ring-shaped for simplicity, but it will be understood by those skilled in the art that other band shapes are possible. As can be seen in FIG. 4, the cross section of the portions 38 of the band 30 disposed through the sleeves 44 in this preferred embodiment are substantially circular. For a desired deployed opening of approximately 2.5 inches in diameter, a polypropylene band 30 having an outside ring diameter of 2.5 inches and a circular cross-sectional diameter of 0.103 inches provides adequate resilience and stiffness. It will be understood by those having skill in the art that the present invention may include larger or smaller pouches 22 requiring correspondingly larger or smaller bands 30. It will also be understood that other cross-sectional configurations are possible such as a rectangular cross-section, which results in a belt-like band 30.

Returning to FIG. 1, the introducer 40 is formed as a thin-walled tube 46 preferably of a substantially transparent medical grade plastic. The introducer 40 has a proximal end 43 and a distal end 44 and defines a lumen 42 extending therebetween. The tube 46 is sized so that it may be inserted into a conventional cannula and will accommodate the pouch assembly 20 when in its storage configuration.

The valve assembly 50 is mounted to the proximal end of the introducer 40 and includes a housing 52 defining a passage 54 therethrough and an arrangement 56 for sealing around an instrument inserted into the introducer 40 through the passage 54. The sealing arrangement 56 preferably includes a septum valve 58 or its equivalent. The septum valve 58 is formed as a generally pliant disc and has a central aperture 59. The central aperture 59 has a diameter that is less than the diameter of the smallest surgical instrument that will be inserted through the valve assembly 50 into the introducer 40. When an instrument is inserted through the valve assembly 50, the aperture 59 stretches to allow passage of the instrument while maintaining a seal around the body of the instrument. The valve assembly 50 thus allows the sealed insertion of a grasping instrument into the introducer 40 for engagement with the pouch assembly 20 for deployment or retrieval of the pouch assembly 20 as will be described in more detail hereafter.

As illustrated in FIGS. 2, 3, 4 and 9, the pouch assembly 20 has three primary configurations including a storage configuration, a deployed configuration and a retrieval configuration. In the storage configuration, the band 30 is collapsed so that the sleeves 26 and the portions 38 of the band 30 disposed therethrough are brought into close proximity as shown in FIG. 4. The pouch 22 is rolled or folded in a manner to facilitate deployment and is positioned beneath the collapsed band 30, also as shown in FIG. 4. The pouch assembly 20 is positioned within the lumen 42 adjacent the distal end 44 of the introducer 40 so that the second tab 34 extends out of the introducer 40. The extension of the second tab 34 outside the lumen 42 of the introducer 40 facilitates the grasping of the second tab 34 for removal of the pouch assembly 20 during surgery as will be described in more detail hereafter. It will be appreciated that the transparent nature of the introducer 40 facilitates the loading of the pouch assembly 20 into the introducer 40 as well as inspection of the assembled retrieval device 10 to assure that the pouch assembly 20 is properly installed prior to use.

The deployed configuration is illustrated in FIGS. 2 and 3. In this configuration, the band 30 biases the opening 25 into a generally elliptical form approaching the circular shape that would be assumed by the 36 if unconstrained by the sleeves 26. The pouch 22 is freely suspended from the band 30.

Figure 10:
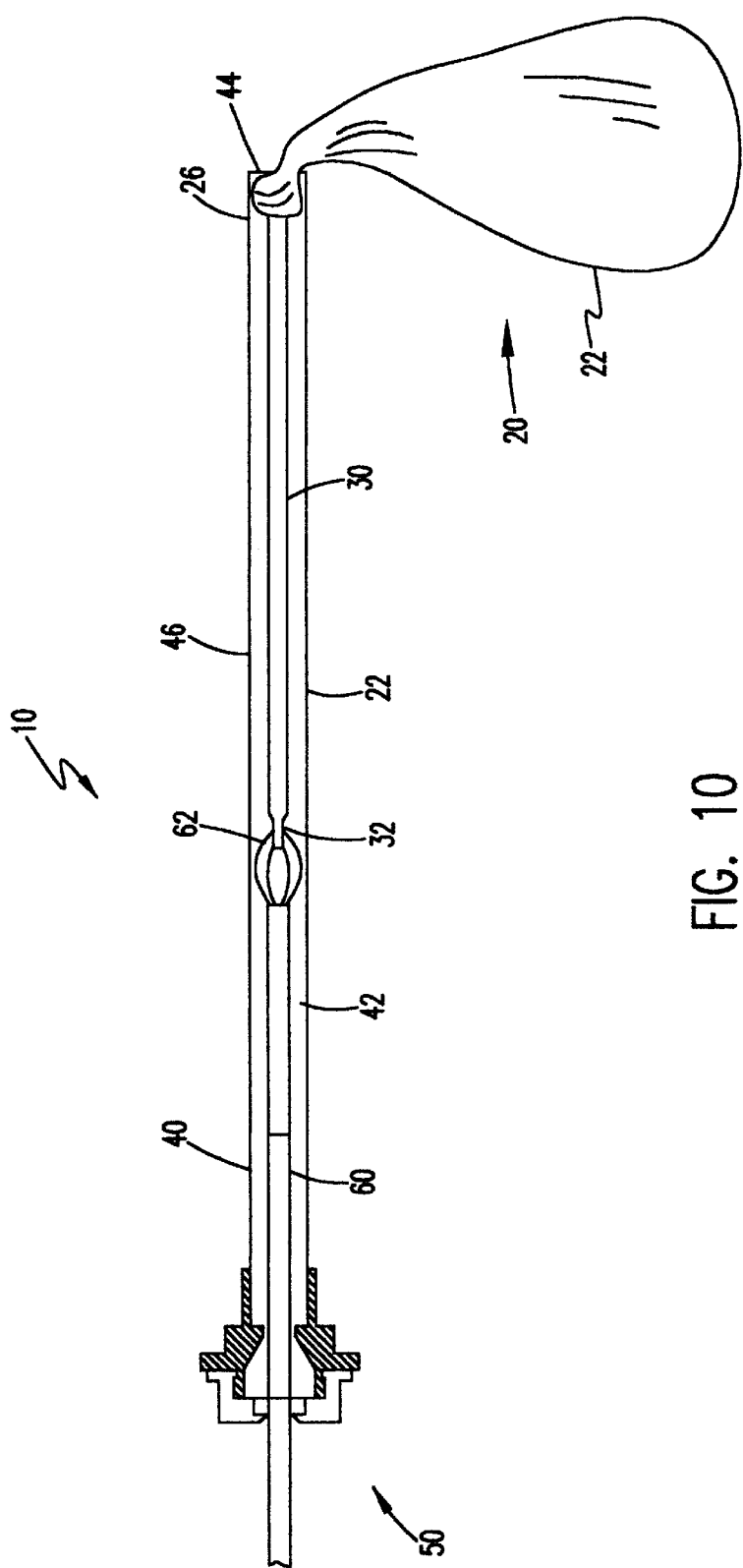
FIG. 10 is a cutaway side view of the specimen retrieval device illustrated in FIG. 1 in a retrieval configuration.

In the retrieval configuration, illustrated in FIG. 10, the band 30 has been withdrawn into the introducer 40 so that its opposite sides are in close proximity as in the storage configuration. In this configuration, however, the sleeves 26 have been gathered against the second grasping tab 34, thereby sealing the opening 25 of the pouch 22, and have been retracted into the distal end 44 of the introducer 40. The remainder of the pouch 22 and any specimens contained therein remain outside of the introducer 40.

In operation, the specimen retrieval device 10 is used by first disposing the pouch assembly 20 in the lumen 42 of the introducer 40 with the pouch assembly 20 in its storage configuration. The distal end 44 of the introducer 40 is inserted through a cannula that has been previously inserted into an incision to permit communication with a body cavity. The introducer 40 is positioned so that its distal end 44 is outside the cannula within the body cavity.

Once the introducer 40 is in position, the pouch assembly 20 may be removed from the introducer 40 using one of two methods. In the first method, the pouch assembly 20 is pushed out of the introducer 40 using any blunt instrument that may be inserted through the valve assembly 50 and into the lumen 42 of the introducer 40 and that is long enough to reach the distal end 44 of the introducer 40. The method is accomplished by simply inserting the blunt instrument (not shown) through the valve assembly 50 into the lumen 42 until it makes contact with the pouch assembly 20. Once having made contact, the instrument is used to push the pouch assembly 20 out of the distal end 44 of the introducer 40.

Figure 5:
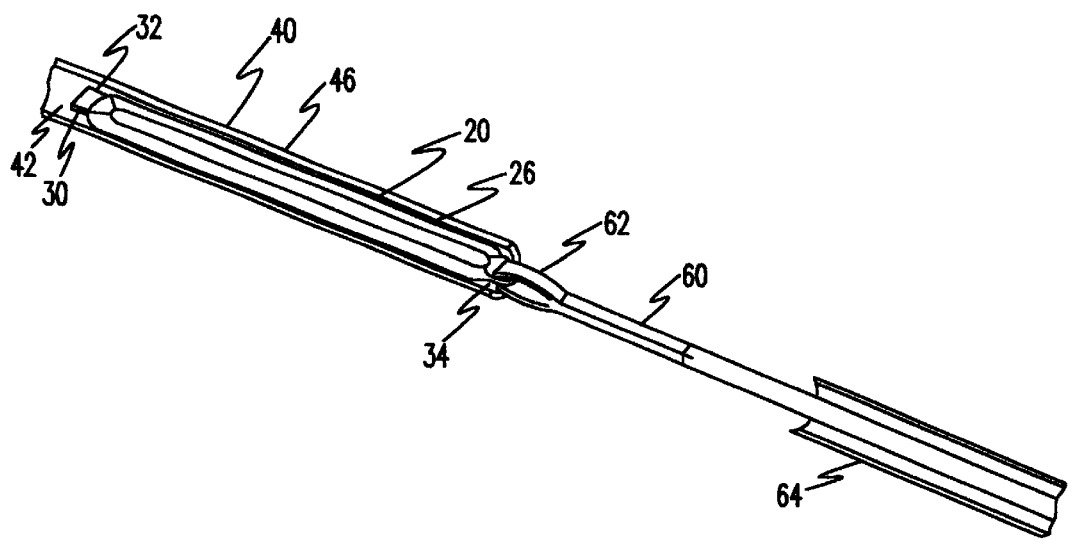
FIG. 5 is a cutaway perspective view of the specimen retrieval device illustrated in FIG. 1.

The second manner in which the pouch assembly 20 may be removed from the introducer 40 involves the use of a grasping instrument 60 inserted through a second cannula 64 as shown in FIG. 5. The grasping element 62 of this instrument is inserted into the body cavity through the second cannula 64 to grasp the second tab 34 extending from the distal end 44 of the introducer 40. Once the second tab 34 has been grasped, the grasping instrument is retracted toward the cannula 64, thereby pulling the pouch assembly 20 out of the introducer 44. It will be understood by those having ordinary skill in the art that the extension of the second tab 34 outside the lumen 42 eases the task of locating and grasping the tab 34. However, it will also be understood that some grasping instruments could be used that would allow the second tab 34 to be grasped even if disposed entirely within the introducer 40. With these instruments, the second tab 34 need only be adjacent the distal end of the introducer 40. The transparent nature of the introducer 40 is of particular value when the tab 34 does not extend outside the introducer 40.

Upon removal of the pouch assembly 20 by either method, the band 30 causes the pouch 22 to open as the band 30 or a portion thereof is removed from the introducer 40. The resilience of the urethane film used to form the pouch 22 is sufficient to cause the pouch 22 to at least partially unroll or unfold. Biological or other material may then be deposited into the pouch 22. If the pouch 22 has not entirely unrolled or unfolded, the deposition of material into the pouch 22 will cause it to fully deploy.

Figure 6:
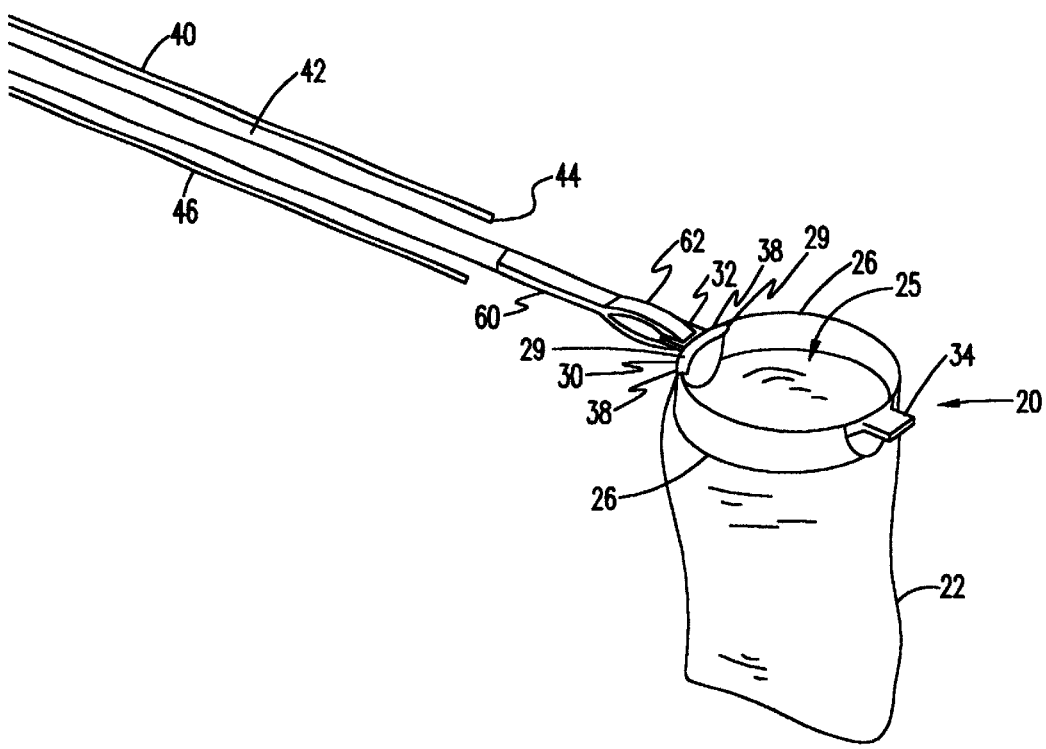
FIG. 6 is a cutaway perspective view of the specimen retrieval device illustrated in FIG. 1 in a deployed configuration.
Figure 7:
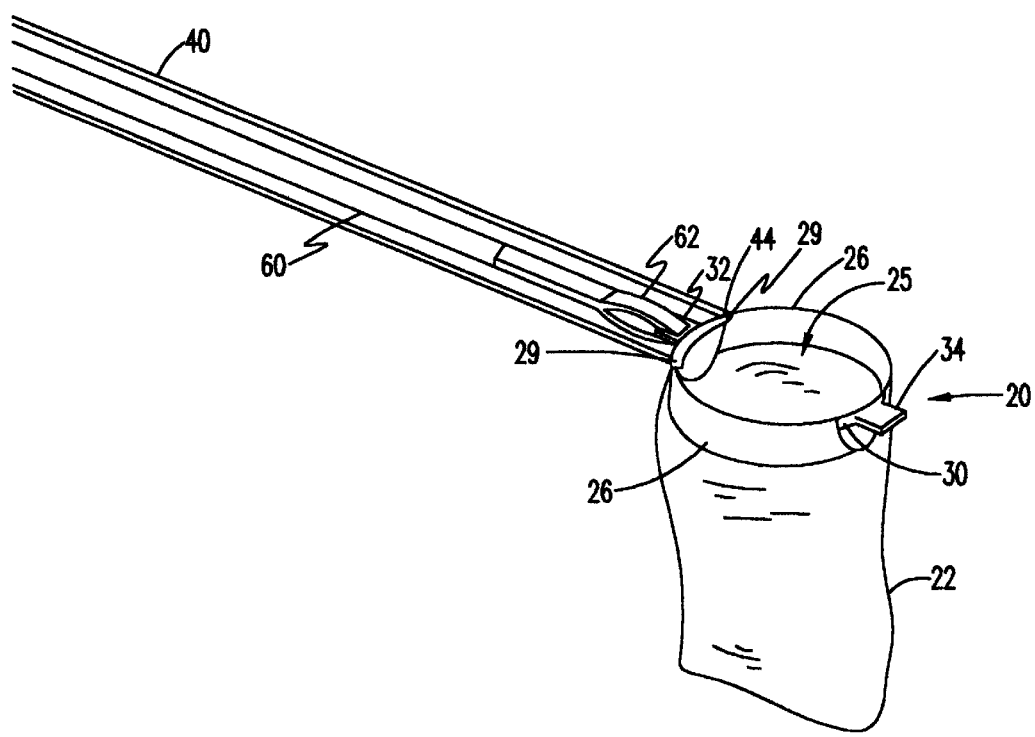
FIG. 7 is a cutaway perspective view of the specimen retrieval device illustrated in FIG. 1 illustrating withdrawal by a grasping instrument.
Figure 8:
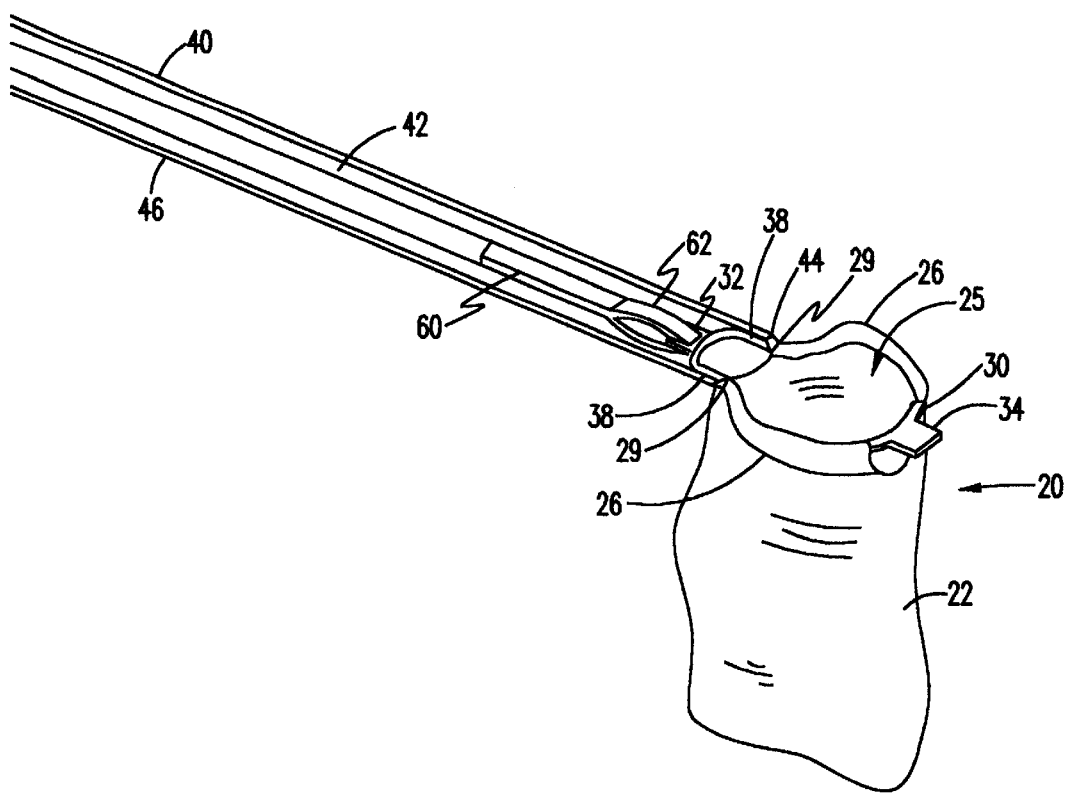
FIG. 8 is a cutaway perspective view of the specimen retrieval device illustrated in FIG. 1 illustrating withdrawal by a grasping instrument.
Figure 9:
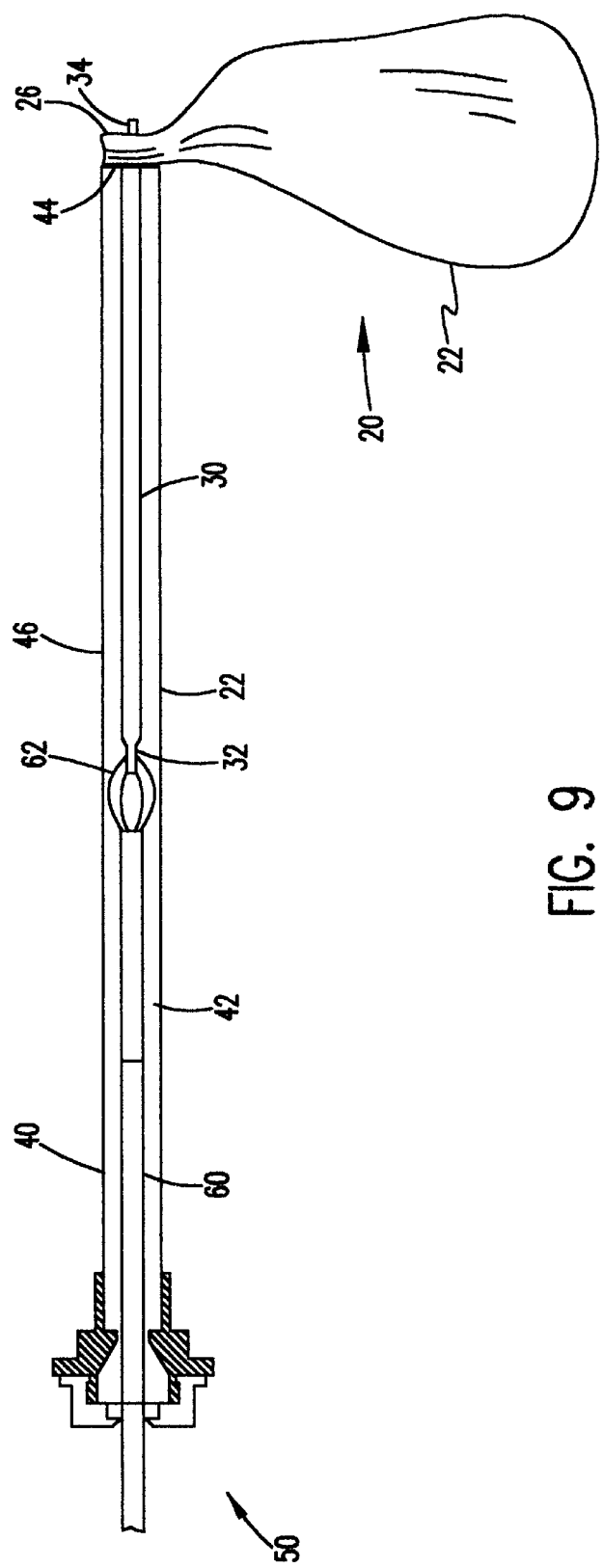
FIG. 9 is a cutaway side view of the specimen retrieval device illustrated in FIG. 1 illustrating withdrawal by a grasping instrument.

Turning now to FIGS. 6 through 9, when the pouch assembly 20 is ready for removal, the grasping element 62 of a grasping instrument 60 is inserted through the valve assembly 50 and the introducer 40 into the body cavity. The grasping element 62 is then used to grasp the tab 32 as shown in FIG. 6. The grasping element 62 is then withdrawn into the lumen 42 of the introducer 40 until the band 30 makes contact with the distal end 44 of the introducer 40 as illustrated in FIG. 7. As shown in FIG. 8, the grasping element 62 is then further withdrawn into the lumen 42 thereby forcing a portion of the band 30 to deform from its elliptical shape and enter the lumen 42. As the band 30 is further drawn into the lumen 42, the distal end 44 of the introducer 40 makes contact with the ends of the sleeves 26 and causes them to draw back along the circumference of the band 30. Importantly, the two sleeves 26 are drawn back independently in a symmetrical manner. This provides a smoother, more reliable gathering of the material surrounding the opening 25 of the pouch 22 than may be obtained using a single continuous sleeve or by withdrawing one side of a band having its other side fixed to the introducer. As the band 30 is yet further drawn into the lumen 42, the band 30 is forced into its retrieval configuration and the sleeves 26 are gathered against the tab 34. This effectively closes and seals the opening 25 of the pouch 22 as shown in FIG. 9. The remainder of the band 30 and the gathered sleeves 26 are then drawn through the distal end 44 into the lumen 42, thereby placing the device 10 in its retrieval configuration as shown in FIG. 10. The introducer 40 and the pouch assembly 20 may then be withdrawn through the cannula. In its retrieval configuration, the pouch 22 is securely closed thus assuring that the specimens enclosed therein cannot escape or be contaminated.

In the method recited above, the introducer 40 may remain in place within the cannula throughout the surgery. However, because the pouch assembly is entirely independent once deployed, the introducer 40 may be removed, making the cannula available for other surgical use. For removal of the pouch assembly 20, the introducer 40 may be reinserted into the cannula and the band 30 retracted into the introducer 40 as previously described. Alternatively, a grasping instrument may be inserted through any available cannula having a distal end of suitable configuration for causing the band 30 to deform to allow the end of the cannula to make contact with the sleeves 26 and gather them together at the second tab 34. To facilitate this approach, a valve assembly similar to the illustrated valve assembly 50 would be attached to the cannula. The introducer 40 could then be inserted through the valve assembly into the cannula and removed from the cannula after deployment of the pouch assembly 20 without loss of body fluids or insufflation pressure. Using this approach, the specimen retrieval device does not require its own valve assembly 50.

The specimen retrieval device 10 of the present invention provides significant advantages over previous devices in its reliability, simplicity and ease of use. Of particular importance is the ease with which the pouch 22 is closed without the use of a tether. The band 30 is configured to deform in such a way as it is withdrawn into the introducer 40 that its opposing side portions 38 are close together and essentially parallel to the common axis of symmetry of the band 30 and the pouch 22 at the entrance to the lumen 42. This reduces the resistance to withdrawal of the band 30 through the sleeves 26. The round cross-section of the band 30 further reduces this resistance by reducing the sliding friction of the sleeves 26 over the band 30. The sleeves 26 are configured to be withdrawn in parallel along the axis of symmetry through the band 30. Simultaneously gathering the sleeves 26 on both sides in this manner results in regular, controlled gathering of the material surrounding the opening 25 and assures secure closure of the pouch 22.

Although a tether is not required for closure of the pouch 22, a retrieval tether (not shown) may be attached to the band 30 and threaded through the introducer 40 to ensure that the location of the pouch assembly 20 within the body cavity may be ascertained or controlled. A retrieval tether could also be used to assist in the process of removal by allowing the surgeon to pull the pouch assembly 20 into a position that facilitates the grasping of the band 30.

By the above, the present invention is shown to provide a low complexity, easily used device for secure removal of tissue or other specimens during surgery.

It will therefore be readily understood by those persons skilled in the art that the present invention is susceptible of a broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiment, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims appended hereto and the equivalents thereof.

I claim:

1. A specimen retrieval device for use within a body cavity during surgery comprising:

an introducer having a proximal end and a distal end and defining a lumen therethrough, said introducer being configured and dimensioned for at least partial introduction into the body cavity through a predefined passageway;

a pouch having an access opening defined therein, said pouch being collapsible for storage within said lumen and expandable upon removal from said lumen, said pouch having a first sleeve formed along a first portion of said pouch adjacent said opening and a second sleeve formed along a second portion of said pouch adjacent said opening, said sleeves being configured to define spacings between said sleeves; and a resilient band having a first band portion slidably disposed within said first sleeve and a second band portion slidably disposed within said second sleeve, said band being configured to be collapsible for storage within said lumen along with said pouch and to bias said pouch in an open configuration when said pouch is removed from said lumen.

2. A specimen retrieval device according to claim 1 wherein said band includes at least one grasping tab projecting from said band and being disposed in one of said spacings, said grasping tab forming a grasping surface for acquisition of said band by a surgical instrument.

3. A specimen retrieval device according to claim 2 wherein said band includes first and second grasping tabs disposed in a spaced relationship along said band and dividing said band into first and second segments intermediate said grasping tabs, said first segment including said first band portion and said second segment including said second band portion.

4. A specimen retrieval device according to claim 1 further comprising means for sealing a surgical instrument inserted into said lumen for interaction with said pouch, said means for sealing being attached to said proximal end of said introducer.

5. A specimen retrieval device according to claim 4 wherein said means for sealing includes a septum valve.

6. The specimen retrieval device of claim 1 wherein said resilient band is not tethered to said introducer.

7. A specimen retrieval device for use within a body cavity during surgery comprising:

an introducer having a proximal end and a distal end and defining a lumen therethrough, said introducer being configured and dimensioned for at least partial introduction into the body cavity through a predefined passageway;

a pouch having an access opening defined therein, said pouch being collapsible for storage within said lumen and expandable upon removal from said lumen, said pouch having a first sleeve formed along a first portion of said pouch adjacent said opening and a second sleeve formed along a second portion of said pouch adjacent said opening, said sleeves being configured to define spacings between said sleeves; and a resilient band having a first band portion slidably disposed within said first sleeve and a second band portion slidably disposed within said second sleeve, said band including first and second grasping tabs disposed in a spaced relationship along said band and dividing said band into first and second segments intermediate said grasping tabs, said first segment including said first band portion and said second segment including said second band portion, and said band being configured to be collapsible for storage within said lumen along with said pouch and to bias said pouch in an open configuration when said pouch is removed from said lumen; and means for sealing a surgical instrument inserted into said lumen for interaction with said pouch, said means for sealing including a septum valve and being attached to said proximal end of said introducer.

8. A method for retrieval of specimens from a body cavity through a predefined passage, said method for retrieval comprising:

providing a specimen retrieval device including an introducer having a proximal end and a distal end and a specimen pouch defining an access opening and having a first sleeve formed along a first portion of said pouch adjacent said opening, a second sleeve formed along a second portion of said pouch adjacent said opening and a resilient band having a first band portion slidably disposed within said first sleeve and a second band portion slidably disposed within said second sleeve, said band being configured to bias said specimen pouch in an open configuration and including at least one grasping tab, said specimen pouch being in a collapsed configuration and removably disposed within said introducer adjacent said distal end;

inserting said introducer into said predefined passage so that said distal end of said introducer extends through said cannula into the body cavity;

removing said specimen pouch from said introducer within said body cavity;

placing material in said specimen pouch for removal from the body cavity;

acquiring said band using a surgical instrument;

withdrawing said band into said introducer through said distal end, thereby gathering said sleeves and closing said opening of said pouch; and withdrawing said introducer and said specimen pouch through said predefined passage.

9. A method for retrieval of specimens according to claim 8 wherein said step of removing said specimen pouch from said introducer includes:

inserting an instrument into said proximal end of said introducer; and pushing said specimen pouch out of said distal end of said introducer thereby releasing said band to open said specimen pouch and allowing said specimen pouch to assume a deployed configuration within the body cavity.

10. A method for retrieval of specimens according to claim 8 wherein said specimen pouch is disposed within said introducer so that one of said at least one grasping tab is disposed adjacent said distal end and wherein said step of removing said specimen pouch from said introducer includes:

inserting a grasping element of a grasping instrument through a second predefined passage into the body cavity;

acquiring said one of said at least one grasping tab of said band using said grasping element;

pulling said specimen pouch out of the distal end of said introducer using said grasping instrument, thereby releasing said band to open said specimen pouch and allowing said specimen pouch to assume a deployed configuration within the body cavity; and releasing said one of said at least one grasping tab.

11. A method for retrieval of specimens according to claim 8 wherein said step of acquiring said band using a surgical instrument includes:

inserting a grasping element of said surgical instrument through said introducer into the body cavity; and acquiring one of said at least one grasping tab of said band using said grasping element.

12. A method for retrieval of specimens according to claim 8 wherein said step of withdrawing said band into said introducer includes:

withdrawing said grasping element into said distal end of said introducer so that said first and second segments of said band make contact with said distal end of said introducer;

further withdrawing said grasping element toward said proximal end of said introducer, thereby forcing said first and second segments to deform and be pulled into said distal end of said introducer, thereby causing said distal end of said introducer to make contact with said first and second sleeves thereby causing said first and second sleeves to slide along said first and second segments away from said one of said at least one grasping tab, thereby causing said opening of said specimen pouch to close; and still further withdrawing said grasping element toward said proximal end of said introducer thereby drawing said sleeves into said introducer.

\* \* \* \* \*